United States Patent [19]

Constien

[11] 4,247,430
[45] Jan. 27, 1981

[54] AQUEOUS BASED SLURRY AND METHOD OF FORMING A CONSOLIDATED GRAVEL PACK

[75] Inventor: Vernon G. Constien, Owasso, Okla.

[73] Assignee: The Dow Chemical Company, Midland, Mich.

[21] Appl. No.: 28,960

[22] Filed: Apr. 11, 1979

[51] Int. Cl.³ ............ C08G 59/14; E21B 43/04; E21B 33/138; C07C 7/18

[52] U.S. Cl. ............ 260/29.2 EP; 166/276; 556/422; 528/27

[58] Field of Search ........... 260/29.2 EP, 448.2 N; 528/27; 166/276

[56] References Cited

U.S. PATENT DOCUMENTS

| | | | |
|---|---|---|---|
| 2,823,753 | 2/1958 | Henderson | 166/20 |
| 3,171,851 | 3/1965 | Pepe | 260/448.2 N |
| 3,477,990 | 11/1969 | Dante | 260/47 |
| 3,496,139 | 2/1970 | Markovitz | 528/27 |
| 3,621,915 | 11/1971 | Bruist et al. | 166/276 |
| 3,854,533 | 12/1974 | Copeland | 166/276 |
| 3,857,444 | 12/1974 | Copeland | 166/276 |
| 3,867,986 | 2/1975 | Copeland | 166/276 |
| 3,931,109 | 1/1976 | Martin | 260/47 EP |
| 3,948,855 | 4/1976 | Perry | 260/47 EP |
| 3,949,140 | 4/1976 | Biefeld et al. | 260/448.2 N |
| 4,042,032 | 8/1977 | Anderson et al. | 166/276 |
| 4,048,141 | 9/1977 | Doorakian et al. | 260/47 EC |
| 4,074,760 | 2/1978 | Copeland et al. | 166/276 |
| 4,081,030 | 3/1978 | Carpenter et al. | 166/276 |
| 4,101,760 | 7/1978 | Copeland et al. | 260/13 |
| 4,113,015 | 9/1978 | Meijs | 166/276 |

OTHER PUBLICATIONS

World Oil, Nov. 1974, Jun. 1965, Part 7, Suman.

*Primary Examiner*—V. P. Hoke
*Attorney, Agent, or Firm*—L. Wayne White

[57] ABSTRACT

An aqueous based slurry is described comprising (1) a thickened water-based carrying fluid, (2) a particulate solid, e.g., gravel, and (3) a resin system comprising an epoxy resin and a novel crosslinking agent. The crosslinking agent is a polymethylene polyphenylamine bearing one or more silane groups of the formula

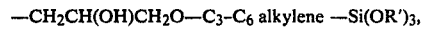

$-CH_2CH(OH)CH_2O-C_3-C_6 \text{ alkylene} -Si(OR')_3$, wherein each R' independently is hydrogen or lower alkyl. This pumpable slurry is suitable for use in emplacing a permeable, consolidated gravel pack between the casing of a well and an incompetent subterranean formation. The slurry is easily formed on site by merely blending the components in an appropriate ratio using conventional equipment.

13 Claims, No Drawings

AQUEOUS BASED SLURRY AND METHOD OF FORMING A CONSOLIDATED GRAVEL PACK

BACKGROUND OF THE INVENTION

The invention pertains to an aqueous-based slurry and a method of emplacing a resin consolidated pack of particulate material between the casing of a well and an unconsolidated formation. The invention also pertains to novel substituted aromatic amines which are useful, for example, as epoxy crosslinking agents in said slurry.

Production of detritus in wells which penetrate unconsolidated, i.e., incompetent, subterranean formations, is an ever present problem, particularly in the petroleum industry. A good discussion of the problem, and of the various techniques used to minimize concurrent production of such detritus can be found in an eight part series by George O. Suman, Jr., appearing in *World Oil* from November, 1974, through June, 1975. The series was published in 1975 as a reprint by Gulf Publishing Co., under the title "World Oil's Sand Control Handbook," the teachings of which are expressly incorporated herein. Three commonly used methods are (1) gravel packing, (2) plastic in situ consolidation, and (3) consolidated packing with a particulate material, often called consolidated gravel packing especially where the particulate material is sand. The latter technique is discussed in Part 7 of said Handbook, and it is this latter technique to which the present invention pertains.

In the early consolidated gravel packing art, typified by Henderson et al., U.S. Pat. No. 2,823,753, it was taught to precoat a particulate with a resin, suspend the coated particulate in a suitable carrier, and inject the suspension into the borehole.

Precoated particulates have had several drawbacks to overcome. Some precoated particulates were not sufficiently stable to be stored and transported without agglomeration. Others which could be handled without an objectionable degree of agglomeration suffered from an inability to form packs having high compressive strengths in low temperature wells, while simultaneously maintaining adequate permeability. Consequently, efforts were generally concentrated on developing high particulate concentration oil based slurries which could be prepared without precoating the particulate prior to admixture with the carrier, and in maximizing the strength and permeability parameters of such systems.

Oil based systems also suffered from numerous inherent disadvantages. In offshore operations, any unused oil carried slurry had to be transported back to shore, and even on land, disposal in an ecologically acceptable manner presented a problem. This, and high inventory costs adversely affected the economics of the treatment, particularly in periods of tight supply. Safety risks were somewhat greater with large quantities of combustible material at the well site and quality control was a problem. Some sources of bright stock oil have such high levels of cationic contaminants that poorly consolidated packs can result, even after attempts to neutralize the effect of such contaminants by best available technology, such as by implementation of the teachings at column 4, line 60 et seq. of Copeland, U.S. Pat. No. 3,867,986. Numerous handling problems were also associated with the oil-based systems (due to this high viscosity and friction loss) which made well operators reluctant to use oil carried systems in gas wells because of concern of possible formation damage by injection of heavy oils and/or excessive pressures at the well head. As a result, the fracturing technique taught by Gurley et al. in U.S. Pat. No. 3,854,533 could not always be implemented safely. Finally, the sensitivity of oil-carried systems to water based fluids required careful handling prior to injection, and the use of oil as a displacing fluid or the use of a wiper plug to separate the slurry from a water-based displacement fluid.

A substantial advancement in the art was made by Copeland et al., in U.S. Pat. No. 4,074,760 and U.S. Pat. No. 4,101,474, in which they described an aqueous based slurry containing an aqueous carrier fluid, an epoxy resin, a curing agent for the resin, a solvent for said resin and curing agent, a finely divided particulate material, a particular quaternary ammonium halide, and a coupling agent to promote bonding of the resin to the particulate.

Carpenter et al., in U.S. Pat. No. 4,081,030 described a further improvement over Copeland et al. Carpenter et al. included certain chelating agents in the carrier fluid which made it less sensitive to polyvalent metal cations which are normally encountered under conditions of use. Such cations can adversely affect the performance of the gravel pack.

The disclosures of the Copeland et al., and Carpenter et al. patents are incorporated herewith by reference.

SUMMARY OF THE INVENTION

A new aqueous slurry has been discovered which is particularly useful for forming a permeable, consolidated gravel pack adjacent to an incompetent subterranean formation in an oil and/or gas-producing well. The slurry comprises (1) an aqueous based carrying fluid, (2) a particulate solid, and (3) a novel epoxy resin system.

This novel epoxy resin system comprises (a) an epoxy resin bearing, on the average, more than one vicinal epoxy group per resin molecule, and (b) a novel crosslinking agent of the formula

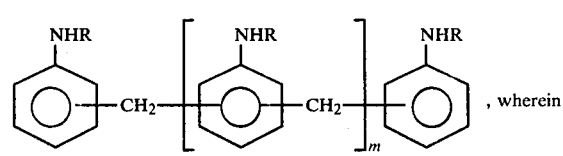

m is from 0 to about 10; each R independently is H or Y provided that at least one R is Y; and Y is

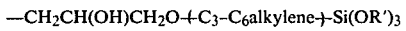

and each R' independently is hydrogen or lower alkyl.

The novel epoxy resin system has an affinity for minerals, and particularly siliceous materials. Therefore, in addition to being useful in making the above slurry for a "gravel pack" application, the epoxy resin system can also be used in making composite structures with mineral extenders or fillers. For example, laminate structures of fiber glass reinforced epoxy resin can be formed.

The components of the slurry are easily blended on site to form a pumpable slurry. The uniformity of the slurry, its ease of preparation, and its characteristics during the pumping operation in a gravel pack operation represent a substantial improvement in the art and add a high degree of quality control.

DETAILED DESCRIPTION OF THE INVENTION

The Resin System

The binder resin used herein is an epoxy resin which bears, on the average, more than one terminal or pendant 1,2-epoxy group per resin molecule.

The epoxy equivalency of such compounds is, therefore, greater than one. The meaning and test for epoxy equivalency is described in U.S. Pat. No. 2,633,458. Various examples of epoxy resins (alternatively known as polyepoxides) that can be used in the present invention are shown in U.S. Pat. Nos. 2,633,458; 3,477,990; 3,931,109; 3,948,855; 4,101,474; 4,048,141, and in the texts: "*Handbook of Epoxy Resins*" by H. Lee and K. Neville, McGraw-Hill Book Co. (1967) and "*Epoxy Resins-Chemistry and Technology*", Edited by C. May and Y. Tanaka, Marcel Dekker, Inc., N.Y. (1973), the disclosures of which are incorporated by reference. The glycidyl ethers of polyhydric phenols are the best known epoxy resins, from a commercial standpoint, and therefore preferred, and the subclasses of compounds represented by formulas II and III are more preferred.

The first subclass corresponds to the formula:

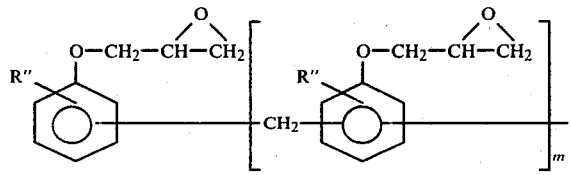

wherein R" is hydrogen or an alkyl radical, preferably hydrogen; and m is from about 0.1 to about 10, preferably from about 1 to about 2. Preparation of these polyepoxides is illustrated in U.S. Pat. No. 2,216,099 and 2,658,885. The second subclass corresponds to the general formula:

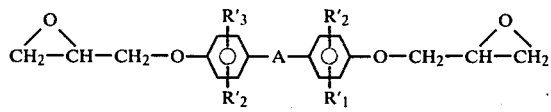

wherein $R'_1$, $R'_2$, $R'_3$ and $R'_4$ are independently selected from hydrogen, bromine and chlorine and wherein A is a single covalent bond or an alkylene (e.g., methylene) or alkylidene (e.g., isopropylidene) group having from about 1 to about 4 carbon atoms, or A is a divalent radical of the formulas:

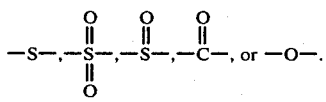

When used in a gravel pack operation, the epoxy resin is included in the resin system in an amount sufficient to coat the particulate solid material in the slurry and will, obviously, vary depending upon the particle size, porosity, etc., of the material being coated. Amounts of epoxy resin beyond that required to coat the particles is normally undesirable because excess resin can adversely affect the permeability of the cured pack, can cause formation damage, and can also make it difficult to remove the portion of the cured pack in the well bore. It will be understood that in this system, or in most multi-component systems, optimization may be required because the limits of operability for one component depend to some extent on other components in the system. Optimization will not require any undue experimentation on the part of a skilled artisan. For example, somewhat less resin can be employed where the total surface area of the particulate is relatively small. Generally, however, an effective slurry is obtained by employing from about 2 to about 10 percent, and preferably from about 3 to about 7 percent of epoxy resin, based on the weight of the particulate material employed. More preferably the resin is employed in an amount ranging from about 3.5 to about 5.5 weight percent of the particulate.

In the gravel pack application, the epoxy resin is normally dissolved in an inert organic solvent and the solution added directly to the gravel pack slurry. Suitable solvents include, for example, aromatic hydrocarbons, alcohols, esters, ethers, ketones, and the like, and mixtures thereof. Specific solvents include, for example, toluene, xylene, isopropanol, n-butanol, ethyl acetate, methyl propionate, ethylene glycol mono-n-butyl ether, diethylene glycol monomethyl ether, diethylene glycol mono-n-butyl ether, methyl ethyl ketone, and the like. Suitable combinations of solvents include, for example, xylene/ethylene glycol monoethyl ether, toluene/ethylene glycol monoethyl ether, and the like. When employed with a resin of the bisphenol-A/epichlorohydrin type, a preferred embodiment is to employ from about 20 to about 75 parts of the aforementioned xylene/ethylene glocol ethyl ether combination of solvents per 100 parts by weight of resin. Selection and optimization of a solvent system is within the skill of the art.

Curing Agent

The novel curing agents correspond to formula I

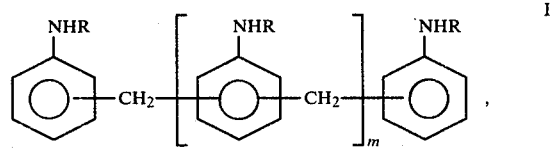

wherein: m is from 0 to about 10, and preferably from 0 to about 4; each R independently is H or Y provided that at least one R is Y; and Y is

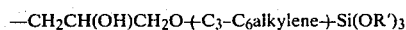

and each R' independently is hydrogen or lower alkyl, and is preferably methyl or ethyl and is more preferably methyl.

The crosslinking agent of formula I is conveniently prepared by reacting an aromatic amine of formula IV

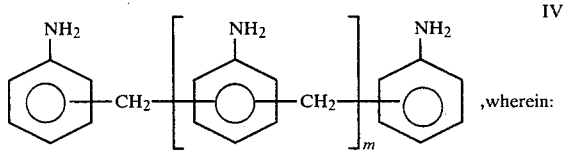
,wherein:

m has the aforesaid meaning, with an epoxy silane of formula V

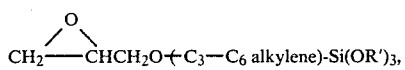

wherein each R' independently is hydrogen or lower alkyl and is preferably methyl or ethyl, and is more preferably methyl.

The reaction is conducted by merely blending reactants IV and V together in liquid phase and under conditions sufficient to promote the reaction. The ratio of reactants can be varied from a substantial excess of IV up to one equivalent weight of IV per mole of V, based on the number of primary amino groups on IV. The reaction product of excess aromatic amine IV and the epoxy silane V is preferred because the excess of IV is also compatible in the epoxy resin system and it also functions as a crosslinking agent. The temperature of the reaction is likewise not critical as long as it is sufficient to promote the desired reaction at a reasonable rate and is below the thermal decomposition temperature of the reactant or reaction product and below the temperature at which the epoxy silane autopolymerizes. Normally, an acceptable rate of reaction is achieved at a reaction temperature of from about 60° C. to about 85° C. The reaction is also conducted under substantially anhydrous conditions due to the susceptibility of the epoxy silane V to hydrolyze. Epoxy silane reactants used in the preparation of I are normally selected such that R' is other than hydrogen. After the product I is formed, the degree of hydrolysis of the silane substituent is not particularly important and stringent efforts to prevent hydrolysis are not required.

The aromatic amine reactants IV are a known class of compounds. They are normally obtained from commercial sources as a mixture of polymethylene polyphenyleneamines, each component of which corresponds to formula IV but with different values for m. As a result, product I likewise is a mixture of compounds of formula I in which m is varied. Such mixtures are preferred due to the commercial availability of the starting material IV and to the fact that such mixtures are normally liquid rather than solid.

The epoxy silane reactants V are likewise a known class of compounds. Those members in which the ($C_3$–$C_6$alkylene) group is a —$CH_2CH_2CH_2$— group are best known from a commercial standpoint and are thus preferred.

The crosslinking agents I can be used alone or in combination with other compatible curing agents. Examples of such compatible curing agents include, for example, aliphatic, cycloaliphatic, aromatic, and heterocyclic polyamines, such as the polymethylene polyphenyleneamines IV, ethylenediamine, diethylenetriamine, triethylenetetraamine, dimethylaminopropylamine, diethylaminopropylamine, piperidine, triethylamine, benzyldimethylamine, N,N-dimethylaminopyridine, 2-(N,N-dimethylaminomethyl)phenol, tris(dimethylaminomethyl)phenol, and the like. Such amino-containing curing agents are well known. See, for example, the texts by Lee et al. and May et al., cited above and U.S. Pat. No. 3,477,990 at column 8, lines 32–60.

The amount of compound I included in the resin system can be varied when used in a gravel pack operation. A sufficient quantity of compound I, or a mixture of I and another compatible crosslinking agent(s), will be used to provide the desired degree of crosslinking and a good bond between the crosslinked (i.e., cured) epoxy resin and the particulate mineral solid. Normally, the curing agent used is a mixture of I and IV having from about 3 to about 85 percent by weight of I; and this mixture used in the epoxy resin system in an amount of from about 10 to about 60 by weight. In the gravel pack application, a solution comprising I in suitable inert organic solvent is likewise added directly to the gravel pack slurry.

Aqueous Carrier Fluid

The carrier fluid employed in the gravel pack application is an aqueous based liquid. It may be water or a brine, e.g., an aqueous solution comprising one or more alkali metal halides. Generally, a brine is preferred since it is more likely to be compatible with connate water which may be present in the formation. Other ingredients can also be included in the carrier fluid if desired. For example, chelating agents, pH control agents, surfactants, viscosity control agents, breakers, etc.

A viscosity builder (a gelling agent) is generally added to improve the solids carrying capacity of the slurry. A slurry with good carrying capacity is normally obtained when the aqueous carrier fluid has a viscosity of from about 90 to about 350 centipoise; and a preferred viscosity is from about 125 to about 160 centipoise at 25° C. An excessively gelled carrier fluid can result in a poorly consolidated pack.

The viscosity builders are a known class of compounds. Examples of which include: natural gums, such as guar gum and other galactomannans, and derivatives and modifications thereof, such as hydroxyalkyl guars; cellulosic derivatives, such as cellulose ethers and particularly hydroxyethylcellulose; water soluble derivatives of starch; polyacrylamide and derivatives thereof; polyvinyl alcohol; and the like. A specific example of a suitable aqueous carrier is one containing about 0.5–0.80 weight percent hydroxyethylcellulose in fresh water or in a brine solution (e.g., 1 to 3 weight percent alkali metal halide). Compatible pH control agents and viscosity breakers may also be included, if desired, to promote the functioning of the gelling agent. Viscosity breakers may be included to rapidly reduce the carrying fluid viscosity once the gravel slurry is placed and thus facilitate the well's return to production, especially where the initial viscosity of the gelled aqueous fluid is high. Various gel breakers are well known and include, for example, enzyme breakers, inorganic breakers and organic breakers.

The aqueous carrier also generally contains a surfactant to aid in the wetting of the siliceous materials. The surfactants used are known classes of cationic surfactants corresponding to formula VI, VII and VIII

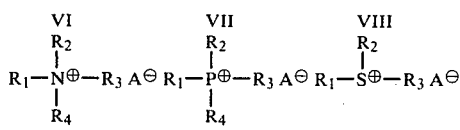

wherein $R_1$ is a hydrophobic organic group of at least seven carbon atoms, and is preferably benzyl or an alkylated benzyl group of from 7 to about 25 carbon atoms; $R_2$ and $R_3$ are each independently lower alkyl or 2-hydroxy (lower alkyl), and are preferably 2-hydroxyethyl with the proviso that at least one of $R_2$ and $R_3$ is 2-hydroxyethyl; and $R_4$ is a 2-hydroxyethyl alkyl group or alkyl of from 1 to about 18 carbon atoms; and $A^\ominus$ is an anion. Surfactants of formula VI are preferred, based on commercial availability. Suitable surfactants include, for example, benzyl-bis(2-hydroxyethyl)-methylammonium chloride, benzyl-bix(2-hydroxyethyl)-octadecylammonium chloride, 4-t-butylbenzyl-bis(2-hydroxyethyl)-methylammonium chloride, 4-dodecylbenzyl-(2-hydroxyethyl)-dimethylammonium chloride, 3,5-dimethylbenzyl-bis(2-hydroxyethyl)-decylammonium chloride, and the like, and the corresponding bromide, phosphate, acetate, propionate, benzoate and picrate salts, and the like, and the corresponding phosphonium salts; and sulfonium salts, such as 4-octylbenzyl bis(2-hydroxyethyl)sulfonium chloride, 4-dodecylbenzyl bis(2-hydroxyethyl)sulfonium chloride, and the like. Mixtures of cationic surfactants or cationic and nonionic surfactants can also be used.

The aqueous carrier fluids described by Copeland et al. and Carpenter et al. are suitable in most instances.

Experimental

Preparation of the Crosslinking Agent/Coupling Agent Adduct

A 500 ml 3-neck flask equipped with a paddle stirrer, reflux condenser, heating means, thermometer and temperature controlling device, was charged with 150 g of polymethylene polyphenylamine (Jeffamine ® AP22 from Jefferson Chemical Company) and 54 g of 3-glycidoxypropyltrimethoxysilane. This ratio of reactants provided 2.91 equivalents of the aromatic amine per 0.23 moles of epoxy silane. The reaction flask was purged with dry nitrogen and the temperature raised to 70° C. and maintained at that temperature with stirring for 5 hours. The progress of the reaction was monitored by removing small samples from the reaction flask, diluting the sample to 60% non-volatiles with ethylene glycol monoethyl ether and measuring the disappearance of silane using a dual column gas chromotograph. At the end of 5 hours at 70° C., a charge of ethylene glycol monoethyl ether (108 g) was fed into the flask and the product cooled to room temperature. A solution of the product was thus formed which was chemically stable but had a tendency to darken upon exposure to light.

Preparation of Carrying Fluid

A carrying fluid was prepared by dissolving 72 g of potassium chloride in 3 liters of tap water. Hydroxyethyl cellulose (19.8 g) was dissolved with stirring in this brine. The sodium salt of ethylenediaminetetraacetic acid (4.8 g) was then added and stirring continued until the maximum viscosity of 140 centipoise (cps) was reached. At the point of maximum viscosity, 30 ml of a commercial quaternary ammonium surfactant was blended into the carrying fluid. The surfactant corresponds to the formula

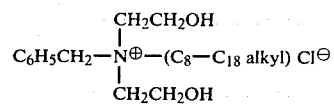

Preparation of Gravel Slurries

A graded sand (20–40 mesh; 360 g) was mixed with 167 g of the above carrying fluid. To this slurry was added with efficient blending 7.9 ml of the above crosslinking agent/coupling agent adduct and 17.9 ml of a solution of a commercial epoxy resin (essentially the diglycidyl ether of bisphenol A; 80% weight percent) dissolved in ethylene glycol monoethyl ether (8.0% weight percent) and xylene (12.0% weight percent).

The order of addition of the slurry components is not critical, but the above procedure is convenient and normally used. Optional components, such as accelerators (e.g., dimethylaminomethyl phenol), viscosity breakers, etc., can be added to the slurry as desired.

From a commercial standpoint, the capabilities offered by this invention by adding individual solutions of the epoxy resin and crosslinking agent/coupling agent directly to the slurry in the mixing vessel without premixing the epoxy resin and crosslinking agent represents a substantial process advantage over the prior art.

Laboratory Screening Test

A standard 50 cc syringe was modified by placing a fine screen across the bottom of the chamber to prevent particulate matter from exiting the port and the syringe was then loaded with the above slurry. The syringe chamber had an internal diameter of essentially 1 inch. The syringe piston was then put in place and depressed at two different rates; first at a rate such that liquid flowed from the syringe at a dropwise manner and second at a substantially higher compaction pressure of approximately 40 to 50 pounds per square inch. The syringe and its compressed contents were then placed in a constant temperature bath for curing at 75° F. for 72 hours or 180° F. for 6 hours. The cured slug was removed from the syringe, cut to a length of about 1.25 inches, and subjected to compressive strength tests measured at the cure temperature. The compressive strength of the cured material was approximately 3450 pounds per square inch at 75° F. and 3080 pounds per square inch at 180° F. This compressive strength is excellent. The cured sample had excellent permeability to water, brines, and oil. Photomicrographs of the cured sample indicated that the sand particles were uniformly coated with the organic coating.

Substantially similar results were achieved when the ratio of epoxy silane to aromatic amine was varied in a series of experiments from about 0.005 to about 0.52 moles of epoxy silane per NH equivalent. This series of experiments showed, however, that the experiment detailed above was at substantially the optimum ratio of reactants in forming the coupling agent adduct. The compressive strength of the cured materials decreased to approximately 2600 pounds per square inch at 75° F. at the extremes of the range. Photomicrographs of the cured samples showed, however, that the sand particles were likewise uniformly coated with the organic coating. The organic coating was crosslinked but the crosslinked density varied.

Gravel packs having excellent compressive strengths and permeability were obtained in substantially the same way except replacing the sand with sintered bauxite, diamonite and glass beads. Other such minerals and siliceous materials can be used in the preparation of the gravel packs.

What is claimed is:

1. A compound corresponding to the formula

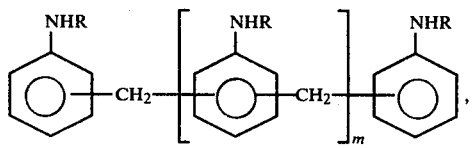

wherein m is from 0 to about 10; each R independently is H or Y provided that at least one R is Y; and Y is

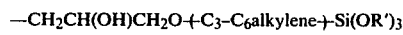

and each R' independently is hydrogen or lower alkyl.

2. The compound defined by claim 1 wherein Y is

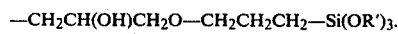

3. The compound defined by claim 1 or claim 2 wherein each R' independently is hydrogen, methyl or ethyl.

4. The compound defined by claim 3 wherein m is from 0 to about 4.

5. A composition comprising (A) a compound corresponding to the formula

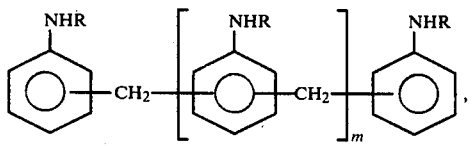

wherein m is from 0 to about 10; each R independently is H or Y provided that at least one R is Y; and Y is

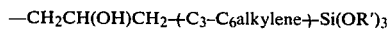

and each R' independently is hydrogen or lower alkyl, and (B) a compound corresponding to the formula

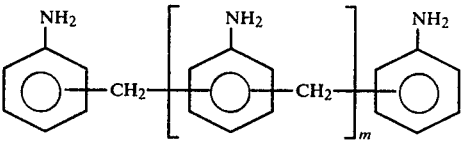

wherein m has the aforesaid meaning.

6. A thermally curable composition comprising a cross-linking amount of the composition defined by claim 5 and (C) an epoxy resin having, on the average, more than one 1,2-epoxy group per resin molecule.

7. The composition defined by claim 6 additionally comprising (D) a particulate solid.

8. The composition defined by claim 7 wherein (D) is sand and/or gravel.

9. The composition defined by claim 8 wherein (D) is sand of uniform or substantially uniform particle size.

10. The composition defined by claim 6 wherein (D) is glass fiber.

11. A pumpable gravel pack slurry composition comprising the composition defined by claim 7, 8 or 9 and a thickened water-based carrying fluid.

12. In the method of emplacing a permeable consolidated gravel pack between the casing of a well and an incompetent subterranean formation by pumping a pumpable gravel pack slurry into position and letting said gravel pack cure in situ, the improvement comprising using the composition defined by claim 11 as the gravel pack slurry composition.

13. The method defined by claim 12 wherein said pumpable gravel pack slurry is formed by blending a thickened water-based carrying fluid with a particular solid, and adding a solution of an epoxy resin having, on the average, more than one vicinal 1,2-epoxy group per molecule and a solution of a composition comprising (A) a compound corresponding to the formula

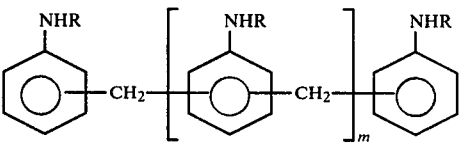

wherein m is from 0 to about 10; each R independently is H or Y provided that at least one R is Y; and Y is
—CH$_2$CH(OH)CH$_2$—(C$_3$–C$_6$alkylene—Si(OR')$_3$ and each R' independently is hydrogen or lower alkyl, and (B) a compound corresponding to the formula

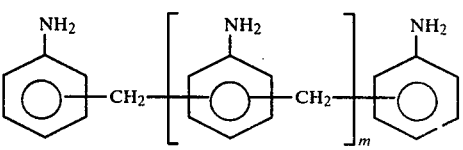

wherein m has the foresaid meaning.

* * * * *

UNITED STATES PATENT AND TRADEMARK OFFICE
CERTIFICATE OF CORRECTION

PATENT NO. : 4,247,430
DATED : Jan. 27, 1981
INVENTOR(S) : Vernon G. Constien

It is certified that error appears in the above—identified patent and that said Letters Patent is hereby corrected as shown below:

In ABSTRACT correct formula to the following:

$-CH_2CH(OH)CH_2O \left( C_3-C_6 \text{ alkylene} \right) Si(OR')_3$ ,

Col. 3, line 40 (second formula) change formula to read as follows:

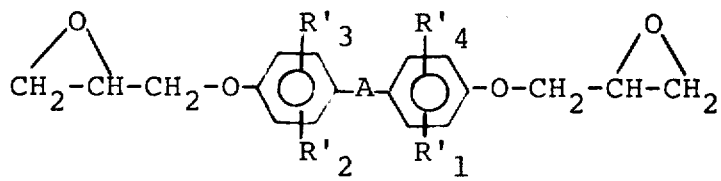

Col. 8, line 25, after "invention" change "by" to --of--.

Col 10, line 49, in the formula after the word "alkylene-" insert a parenthesis [)].

Signed and Sealed this

Fourteenth Day of July 1981

[SEAL]

Attest:

GERALD J. MOSSINGHOFF

Attesting Officer    Commissioner of Patents and Trademarks